United States Patent [19] [11] Patent Number: 5,350,850
Vecchi [45] Date of Patent: Sep. 27, 1994

[54] PROCESS FOR THE PREPARATION OF SUBSTITUTED TETRAHYDROFOLICO DERIVATIVES IN THE [6(R,S)(−)] FORMS AND OF THEIR ACTIVE [6(S)(−)] $N^5$ DIASTEREOISOMERS IN FORM OF ALKALI AND ALKALINE EARTH METAL SALTS

[75] Inventor: Giuseppe Vecchi, Aldesago, Switzerland

[73] Assignee: APR Applied Pharma Research S.A., Lugano, Switzerland

[21] Appl. No.: 957,176

[22] Filed: Oct. 7, 1992

[30] Foreign Application Priority Data

Oct. 10, 1991 [CH] Switzerland .................. 02 986/91-8

[51] Int. Cl.$^5$ ............................................ C07D 475/04
[52] U.S. Cl. .................... 544/258; 544/259; 544/260
[58] Field of Search ................ 544/258, 259, 260

[56] References Cited

U.S. PATENT DOCUMENTS 5,124,452 6/1992 Gennari ............................. 544/258
5,194,611 3/1993 Marazza et al. .................... 544/258

FOREIGN PATENT DOCUMENTS 0189990 8/1986 European Pat. Off. .
635344 2/1978 Switzerland .
1572138 7/1980 United Kingdom .

*Primary Examiner*—John M. Ford
*Assistant Examiner*—Y. N. Gupta
*Attorney, Agent, or Firm*—Nixon & Vanderhye

[57] ABSTRACT

Process for the preparation of the optically active [6(S)(−)]$N^5$ alkaline earth metal salts of methyltetrahydrofolic acid and formyltetrahydrofolic acid wherein an aqueous solution of folic acid is hydrogenated with a high stoichiometric excess of sodium borohydride followed by treating the reaction product with formic aldehyde and optionally further with sodium borohydride when the methyl derivative is desired. Reaction with a salt of the alkaline earth metal precipitates the desired optically active alkaline earth metal salt.

18 Claims, No Drawings

PROCESS FOR THE PREPARATION OF SUBSTITUTED TETRAHYDROFOLICO DERIVATIVES IN THE [6(R,S)(−)] FORMS AND OF THEIR ACTIVE [6(S)(−)] $N^5$ DIASTEREOISOMERS IN FORM OF ALKALI AND ALKALINE EARTH METAL SALTS

The present invention relates to a process for obtaining with optimum yields [6(R,S)(−)]$N^5$ methyltetrahydrofolic acid or [6(R,S)(−)]$N^5$ formyltetrahydrofolic acid isolated as Na,K, Li, Ca, Ba and Mg salts. The invention further relates to a method for the separation of the two R and S forms aiming to obtain the active isomer, [6(S)(−)]$N^5$ methyltetrahydrofolic acid, but this method can be applied as well with good results to other tetrahydrofolic derivatives, differently substituted in the 5 position such as the 5-formyltetrahydrofolic acid and isolated as their salts of divalent inorganic ions.

BACKGROUND OF THE INVENTION

The [6(R,S)(−)]$N^5$ methyltetrahydrofolic acid can be considered as the first conversion metabolite of the [6(R,S)(−)]$N^5$ formyltetrahydrofolic acid and is its biologically active form.

The pharmacological kinetics of the two stereoisomers indicate that they are different since the (6S) isomer is absorbed in the gastrointestinal tract, probably due to a transport carrier, whereas a low biological activity has been assessed for the (6R) isomer.

Moreover the calcium [6(S)(−)]$N^5$ methyltetrahydrofolate by passing the haematoencephalic barrier represents the only form of folate which is actively carried into the central nervous system (CNS); as a matter of fact it is concentrated in the cephalic rachidian liquor and in the synaptic regions.

Furthermore on the basis of several experimental studies it appears that this metabolite is also essential for the synthesis of S-adenosylmethionine in the CNS, by giving its methyl group to the homocisteine to get methionine which is thereafter converted into sulfoadenosylmethionine through the specific enzyme. Such a metabolic relationship between methyltetrahydrofolic acid and S-adenosylmethionine suggests a relevant antidepressive action of the methyltetrahydrofolic acid, since the synthesis of catecholaminic, indolaminic and imidazole neuromediators is promoted, the methylation deficit of the phospholipids in the geriatric age being moreover antagonized; In this manner its potential activity at the hepatocellular level is explained, the methylation processes being made easier also in the presence of hepatopathies.

In view of the above considerations there is foreseen the use of the [6(S)(−)]$N^5$ methyltetrahydrofolic acid in patients suffering of mental deterioration, as regards the induction of the memory and of knowledge functions, the behaviour and affective modifications as well as all that relates to the side symptoms of the pathologies related to the cerebrovascular apparatus of aged persons and of the hepatic malfunctions.

SUMMARY OF THE INVENTION

The purpose of the present invention is to provide an industrially advantageous process for the preparation of [6(R,S)(−)]$N^5$ methyltetrahydrofolic acid and [6(R,S)(−)]$N^5$ formyltetrahydrofolic acids, of their salts with alkali and earth alkali metals as well as for the separation of their pharmaceutically active isomers, namely [6(S)(−)]$N^5$ methyltetrahydrofolic acid and [6(S)(−)]$N^5$ formyltetrahydrofolic acid.

The present invention provides for the preparation of the above mentioned acids the following steps:

a) hydrogenation of an aqueous solution of folic acid with NaBH$_4$, used at the concentrations as indicated hereinafter with respect to the method, in alkaline aqueous solution: the reaction is carried out at a temperature of between 3° C. and 30° C. and for a time of between 5 and 60 minutes for the mixing phase, whereas the reduction step is carried out at a temperature of between 70° C. and 100° C. and for a time of 20 to 30 minutes.

b) reaction of the product from the reaction step (a) with formic aldehyde at a temperature less than 90° C. and then reduction with an alkaline aqueous solution of sodium borohydride at a temperature of the order of 60° C.

c) separation through precipitation of the mixture of inorganic salts by treatment with a strong acid and adjustment of the pH of the resulting solution at a value close to the neutrality, which represents a fundamental feature for obtaining the final product.

As regards the preparation of the salts of earth alkali metals the present invention comprises d) adding to the solution of the step (c) an aqueous solution of a chloride of the desired earth alkali cation, the desired salt being then separated by crystallization at a pH of between 7 and 7.2. Lastly the separation of the desired active isomer is carried out according to the present invention by a process comprising the instantaneous addition to the solution obtained in the previous step (c), maintained at pH 7 and at a controlled temperature of between −5° C. and +10° C., and preferably of between −2° C. and +2° C., a 4M aqueous solution of CaCl$_2$, the calcium salt of the desired isomer, namely calcium [6(S)(−)]$N^5$ methyl or formyl tetrahydrofolate, being then crystallized, this salt being pure and devoid of the R isomer; the precipitated product is in form of a mixture of monohydrate and pentahydrate crystalline forms.

EXAMPLES

More details about the process of the present invention can be obtained from the following exemplifying description of the single process steps.

1. Preparation of the [6(R,S)(−)]$N^5$ methyltetrahydrofolic acid. A 500 liters enameled reactor (A) is used, having a cooling and heating jacket, means being provided for the stirring, for the bubbling of pure nitrogen, together with a thermometer and with means for the possible direct connection with a reactor (B), having a cooling jacket and a stirrer. The reactor (A) is charged with 14 kg of NaBH$_4$ in 17.4 liters of a 20% aqueous solution of NaOH under stirring and keeping the temperature at a controlled level of +20° C.

Then 0.5 kg of disodium salt of ethylendiaminotetraacetic acid (EDTA) are added. In this reaction mixture pure nitrogen is bubbled with a continuous flow and the reaction is continued under these conditions. The internal temperature of the reaction mass is lowered to between 0° C. and +5° C.

60 liters of water are charged in the reactor (B) and under stirring there are added in portions 20 kg of folic acid of the F.U. type, the suspension being vigorously stirred and then the reaction mixture is cooled to +5° C. This solution (B) is poured in the reactor (A) in a time of between 5 and 60 minutes, preferably of between 20 and 30 minutes, taking care that the internal temperature of the reaction is maintained within the 5°-30° C. interval, preferably between 20° C. and 25° C. Upon the addition is completed the reaction mixture is heated up to 90°-95° C. for a time of 20 minutes (step A).

The mixture is cooled to 15° C. and then in about 30 minutes and at a temperature not higher than 20° C. 15.4 liters of 37% HCl are added. The final pH after the pouring is about 9. The temperature is brought back to less than 10° C.

Then in the reactor (A) 9 liters of formic aldehyde are slowly added, the temperature being always maintained to less than 30° C. The reaction is highly hexothermal and the temperature in this step is to be very carefully controlled since it really determines the obtainable final yields. At a reactor temperature of 5° C. the solution present in the reactor (A) is added with a cooled solution of 7 kg of $NaBH_4$ suspended in 10 liters of 0.2N NaOH in water; the addition is to be effected in 20 minutes taking care that the temperature also in this phase is not higher than 20° C.

Upon the addition is completed the mixture is very slowly heated to 60° C. and this temperature is maintained for a 15 minutes time.

The resulting mixture is cooled to $+5°$ C., 9.2 liters of 37% HCl are added and the temperature is maintained for 2 hours at a value below and not higher than 5° C. to let the inorganic salts consisting of borates to be crystallized.

The precipitate of inorganic salts is filtered and the resulting solution is added with about 1.6 liters of 37% HCl so that the pH is between 7.1 and 7.2 (solution X) (step B).

2. Precipitation of $[6(R,S)(-)]N^5$ methyltetrahydrofolates diastereoisomers as calcium salts.

The solution X as above obtained is added with 40 liters of a 2M $CaCl_2$ solution, care being taken of controlling that the final pH is 7 (this fact representing an essential feature for the prosecution of the reaction).

The temperature of this solution is lowered to $+10°$ C. and the product is let to crystallize.

After filtration by centrifugation a recrystallization is carried out in 200 liters of boiling water.

2 kg of active carbon are added, if necessary, and the mixture is filtered. The solution is cooled to $+10°$ C. and the final product is let to crystallize until it is completely precipitated.

The product is filtered and dried in a drier under vacuum avoiding light and contact with oxygen. The yield of the final product is 14 kg.

Like results are obtained in the preparation of the respective Mg and Ba folates, the corresponding chlorides $MgCl_2$ and $BaCl_2$ being used as 32 liters of a 2M solution. The Na, K and Li salts are obtained by using the proper ion exchange resins from Ca, Mg and Ba salts.

3. Precipitation of the active isomer, $[6(S)(-)]N^5$ methyltetrahydrofolic acid as the calcium salt.

The solution X as above obtained in (1) and carefully adjusted to pH 7 and to a temperature of between $+2°$ C. and $-2°$ C. is added in one shot with a solution of 5 liters of $CaCl_2$ in water with a 4M concentration.

The crystallization of the product is very slow and takes place in a time of 4-5 days, the solution being maintained at a constant temperature of between $+2°$ C. and $-2°$ C.

Calcium $[6(S)(-)]N^5$ methyltetrahydrofolate is precipitated as the product in an amount of between 1,800 and 2,200 kg. The product is found pure and devoid of R isomer.

It can be recrystallized from boiling water and has the following chemical and physical characteristics:

Raw formula: $C_{20}H_{23}N_7O_6Ca$ M.W.: 497.55 Aspect: white brown crystalline powder Moisture: 15.27% Solubility: soluble in acids and bases; practically insoluble in water; insoluble in organic solvents. Calcium content: 8.07% HPLC purity: 99.0% U.V. (20 mg/l in 1% $NH_4OAc$/pH 6.0)=290 nm(=28400) max min=245 nm Al/Al=3.7 Stereoisomeric purity: 99.0% (6S)(−)

4. Preparation of the $[6(R,S)(-)]N^5$ formyltetrahydrofolic acid The process is carried out up to the step A as for the methyltetrahydrofolic acid. Then the mixture is made acidic with HCl up to acid pH whereby tetrahydrofolic acid precipitates.

The latter is suspended up to neutral pH and the thus obtained solution is added with formic aldehyde. The mixture is stirred for 2 hours at 10° C., then a stoichiometrical amount of $CaCl_2$ is added and the $[6(R,S)(-)]N^5$ formyltetrahydrofolic acid is crystallized from a solution oversaturated by NaCl.

5. Separation of mixtures of stereoisomers of $[6(R,S)(-)]N^5$ formyltetrahydrofolic acid as the calcium salt of the active isomer, $[6(S)(-)]N^5$ formyltetrahydrofolic calcium salt.

600 g of a mixture of stereoisomers of $[6(R,S)(-)]N^5$ formyltetrahydrofolic acid as the pentahydrate calcium salt are added to 1,500 liters of water under nitrogen stream, the mass being maintained under stirring and at a temperature of between 5° and 10° C.

370 g of EDTA disodium salt are added in portions under stirring at the same time as a 10M solution of sodium hydroxide in stoichiometrical amount with respect to the weighed amount of stereoisomers. The solution is maintained under stirring in these conditions for about one hour, by carefully controlling that the pH of the solution is 7. Then 33 g of anhydrous $CaCl_2$ are added in portions. The pH is controlled at a value of between 6.7 and 7.2.

The solution is made oversaturated by adding NaCl and then is stored in a refrigerator at a temperature of between $-5°$ C. and $+10°$ C., preferably between $+2°$ C. and $-2°$ C.

It is maintained at rest for 4 days and the precipitate is collected in an amount of 120 g of $[6(S)(-)]N^5$ formyltetrahydrofolic stereoisomer. It is recrystallized from ethanol/water and there are obtained 100 g of pure product, having at the HPLC control the chemical and physical properties of the standard sample. The above precedure is repeated until a product having the desired isomeric purity is obtained. By the same process the active stereoisomer $[6(S)(-)]N^5$ methyltetrahydrofolic having the same above mentioned chemical and physical properties can be prepared from mixtures of calcium salts of $[6(R,S)(-)]N^5$ methyltetrahydrofolic acid.

I claim:

1. A process for the preparation of the optically active $[6(S)(-)]N^5$ alkaline earth metal salts of formyltetrahydrofolic acid, said process comprising the steps of:
   a) mixing an aqueous solution of folic acid with a stoichiometric excess of $NaBH_4$ in aqueous alkaline solution at a temperature of 5° C. to 30° C. and for a time period of 5 to 60 minutes;

b) heating the mixture produced in step a) at a temperature of from 70° C. to 100° C. and for a time of 20 to 30 minutes to reduce the folic acid;

c) acidifying the product of step b) to cause tetrahydrofolic acid to precipitate;

d) dissolving the precipitate produced in step c) and reacting the resulting solution with formic aldehyde at a temperature less than 90° C.;

e) treating the product of step d) with a strong acid and adjustment of the pH of the resulting solution to about 7 to cause precipitation of inorganic salts from solution;

f) adding to the solution obtained in step e) an aqueous solution of a salt of an alkaline earth metal salt while maintaining the solution obtained at pH 7 and at a temperature of −5° C. to 10° C.; and g) allowing the optically active [6(S)(−)]$N^5$ alkaline earth metal salt of formyltetrahydrofolic acid to crystallize.

2. A process according to claim 1, wherein in step f) the solution obtained in step e) is maintained at a controlled temperature of between −2° C. and +2° C. and said salt of said alkaline earth metal is calcium, barium or magnesium chloride.

3. A process according to claim 1, wherein in step a) an aqueous solution of folic acid maintained at a temperature of 5° C. is added to a 20% NaOH aqueous solution in which the stoichiometric excess of NaBH$_4$ is dissolved under stirring and is maintained at 20° C.

4. A process according to claim 1, wherein in the NaBH$_4$ is present in least four times the stoichiometric amount.

5. A process according to claim 3, wherein a sodium salt of ethylendiaminotetraacetic acid (EDTA) is added to the mixture of folic acid and NaBH$_4$ and the temperature of the solution is brought to 0° to 5° C.

6. A process according to claim 1, wherein in step a) the temperature is from 20° C. to 25° C.

7. A process according to claim 1, wherein the time period in step a) is 20–30 minutes.

8. A process according to claim 1, wherein step b) is carried out at 90°–95° C. for a period of 20 minutes.

9. A process according to claim 1, wherein in step f) said aqueous alkaline earth metal solution is a 4M aqueous solution of calcium chloride.

10. A process for the preparation of the optically active [6(S)(−)]$N^5$ alkaline earth metal salts of methyltetrahydrofolic acid, said process comprising the steps of:

a) mixing an aqueous solution of folic acid with a stoichiometric excess of NaBH$_4$ in aqueous alkaline solution at a temperature of 5° C. to 30° C. and for a time period of 5 to 60 minutes;

b) heating the mixture produced in step a) at a temperature of from 70° C. to 100° C. and for a time of 20 to 30 minutes to reduce the folic acid;

c) reacting the product of step c) with formic aldehyde at a temperature less than 90° C.;

d) heating the product of step c) with an aqueous alkaline solution of NaBH$_4$ at a temperature of about 60° C.;

e) treating the product of step d) with a strong acid and adjustment of the pH of the resulting solution to about 7 to cause precipitation of inorganic salts from solution;

f) adding to the solution obtained in step e) an aqueous solution of a salt of an alkaline earth metal salt while maintaining the solution obtained at pH 7 and at a temperature of −5° C. to 10° C.; and g) allowing the optically active [6(S)(−)]$N^5$ alkaline earth metal salt of methyltetrahydrofolic acid to crystallize.

11. A process according to claim 10, wherein in step f) the solution obtained in step e) is maintained at a controlled temperature of between −2° C. and +2° C. and said salt of said alkaline earth metal is calcium, barium or magnesium chloride.

12. A process according to claim 10, wherein in step a) an aqueous solution of folic acid maintained at a temperature of 5° C. is added to a 20% NaOH aqueous solution in which the stoichiometric excess of NaBH$_4$ is dissolved under stirring and is maintained at 20° C.

13. A process according to claim 12, wherein a sodium salt of ethylendiaminotetraacetic acid (EDTA) is added to the mixture of folic acid and NaBH$_4$ and the temperature of the solution is brought to 0° to 5° C.

14. A process according to claim 10, wherein in the NaBH$_4$ is present in least four times the stoichiometric amount.

15. A process according to claim 10, wherein in step a) the temperature is from 20° C. to 25° C.

16. A process according to claim 10, wherein the time period in step a) is 20–30 minutes.

17. A process according to claim 10, wherein step b) is carried out at 90°–95° C. for a period of 20 minutes.

18. A process according to claim 10, wherein in step f) said aqueous alkaline earth metal solution is a 4M aqueous solution of calcium chloride.

* * * * *